United States Patent [19]

Marquis et al.

[11] Patent Number: 5,912,382
[45] Date of Patent: Jun. 15, 1999

[54] HYDROXYALKYL CARBAMATE COMPOSITIONS AND PROCESSES FOR MANUFACTURING SAME

[75] Inventors: Edward T. Marquis, Austin; Chris E. Godinich, Houston; Robert E. Baldwin, Georgetown, all of Tex.

[73] Assignee: Huntsman Pertochemical Corporation, Austin, Tex.

[21] Appl. No.: 08/902,617

[22] Filed: Jul. 29, 1997

Related U.S. Application Data

[60] Provisional application No. 60/048,059, May 29, 1997.
[51] Int. Cl.$^6$ .................................................. C07C 261/00
[52] U.S. Cl. ............................................................. 560/166
[58] Field of Search ............................................... 560/166

[56] References Cited

U.S. PATENT DOCUMENTS

| | | | |
|---|---|---|---|
| 2,627,524 | 2/1953 | Malkemus | 260/482 |
| 2,802,022 | 8/1957 | Groszos | 560/166 |
| 2,928,812 | 3/1960 | Ernst | 260/67.5 |
| 2,967,880 | 1/1961 | Finke | 560/166 |
| 3,076,007 | 1/1963 | Barclay | 560/166 |
| 3,703,538 | 11/1972 | Malkemus | 560/166 |
| 5,089,617 | 2/1992 | Forgione et al. | 544/196 |

*Primary Examiner*—Michael L. Shippen
*Attorney, Agent, or Firm*—Arnold White & Durkee

[57] ABSTRACT

High purity hydroxyalkyl carbamates having alkyl groups with two, or three or more carbon atoms may be produced from anhydrous ammonia and alkylene carbonates at relatively low pressures, such as in a low pressure conventional kettle process. In this method, a reactor vessel is typically evacuated prior to reaction and anhydrous ammonia and alkylene carbonates are typically reacted in the presence of an initiator. Using this method, hydroxypropyl carbamate products having a purity greater than about 97%, and hydroxybutyl carbamate products having a purity greater than about 95% may be produced. Hydroxybutyl carbamate compositions comprising mixtures of 2-hydroxylbutyl carbamate and 1-hydroxymethyl propyl carbamate may also be produced.

51 Claims, No Drawings

HYDROXYALKYL CARBAMATE COMPOSITIONS AND PROCESSES FOR MANUFACTURING SAME

This application claims priority on provisional patent application Ser. No. 60/048,059 filed May 29, 1997, entitled "Low Pressure Kettle Process for Manufacture of Hydroxyalkyl Carbamate," by Edward T. Marquis.

BACKGROUND OF THE INVENTION

1. Field of the Invention

This invention relates generally to production of hydroxyalkyl carbamates from anhydrous ammonia and alkylene carbonates. In particular, this invention relates to the low pressure production of high purity hydroxyalkyl carbamates having alkyl groups with three or more carbon atoms by reacting anhydrous ammonia with alkylene carbonates in an evacuated reaction vessel and in the presence of an initiator. This invention also relates to the production of hydroxybutyl carbamate compositions comprising mixtures of 2-hydroxylbutyl carbamate and 1-hydroxymethyl propyl carbamate.

2. Description of the Related Art

Hydroxyalkyl carbamates, such as hydroxylpropyl carbamate and hydroxybutuyl carbamate, are useful intermediates that find utility as, among other things, components in clear topcoats for automobiles. In the past, hydroxyalkyl carbamates have been produced by the reaction of alkylene carbonates with aqueous ammonia or ammonium hydroxide. Although reaction of alkylene carbonates with aqueous ammonia occurs readily, the purity of resulting hydroxyalkyl carbamate products is typically poor due to hydrolysis reactions that occur in the presence of water. Typical hydrolysis byproducts that reduce the purity of hydroxyalkyl carbamate products include alkylene glycols. Because of these impurities, hydroxyalkyl carbamate products produced using aqueous or aqueous ammonia typically have purity levels that do not exceed about 90%. Such low purity levels render hydroxyalkyl carbamate products produced by this method unsuitable for many end uses. In addition, hydroxyalkyl carbamates typically must be isolated by distillation or the like from aqueous reaction products which result from the reaction of alkylene carbonates and aqueous ammonia.

In an attempt to improve the purity of hydroxyalkyl carbamates, reaction schemes employing alkylene carbonates and anhydrous ammonia have been employed. However, reaction between alkylene carbonates and anhydrous ammonia is typically difficult to to initiate, typically requiring elevated pressures. For example, the reaction of propylene carbonate with anhydrous ammonia typically requires a pressure of about 100–200 psig in order to initiate reaction. This pressure range is unsuitable for commercial production in conventional kettle reactor vessels.

SUMMARY OF THE INVENTION

In one respect the invention contemplates a process for preparing a hydroxyalkyl carbamate and a hydroxyalkyl carbamate prepared by the process. The process includes combining an alkylene carbonate with anhydrous ammonia in the presence of an initiator compound at a pressure of less than about 90 psig to form a reaction product that includes hydroxyalkyl carbamate. In this process the alkylene carbonate and anhydrous ammonia may be combined under at least partially evacuated conditions, and the alkylene carbonate may have the formula:

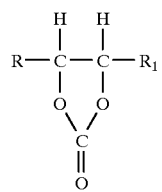

wherein R and $R^1$ are hydrogen or an alkyl, and in which at least one of R or $R^1$ is an alkyl. In one embodiment of this process, alkylene carbonate may be combined with anhydrous ammonia in the presence of an initiator compound at a pressure of less than about 75 psig. In another embodiment, at least a portion of unreacted anhydrous ammonia may be removed from the reaction product to form a hydroxyalkyl carbamate product. In this regard, one embodiment contemplates removing at least a portion of unreacted anhydrous ammonia from the reaction product to form a hydroxyalkyl carbamate product including greater than about 95% by weight of the hydroxyalkyl carbamate, and another embodiment contemplates removing at least a portion of unreacted anhydrous ammonia from the reaction product forms a hydroxyalkyl carbamate product including greater than about 97% by weight of the hydroxyalkyl carbamate. In another embodiment of this process, the combining may occur within a reaction vessel and the alkylene carbonate and the initiator compound may be combined under at least partially evacuated conditions within the reaction vessel prior to combining the alkylene carbonate with the anhydrous ammonia, and the reaction vessel may be at least partially evacuated after combining the alkylene carbonate with the initiator compound in the reaction vessel and prior to combining the alkylene carbonate with the anhydrous ammonia. In another embodiment of this process, the alkylene carbonate may be propylene carbonate and the hydroxyalkyl carbamate may be hydroxypropyl carbamate.

In still another embodiment, the alkylene carbonate may be butylene carbonate and the hydroxyalkyl carbamate may be hydroxybutyl carbamate.

In another respect the invention contemplates a process for preparing a hydroxypropyl carbamate and a hydroxypropyl carbamate prepared by the process. The process includes combining a propylene carbonate with anhydrous ammonia at a maximum pressure of less than about 90 psig to form a reaction product including hydroxypropyl carbamate. In one embodiment of this process, the propylene carbonate may be combined with the anhydrous ammonia at a pressure of less than about 75 psig. In another embodiment, the propylene carbonate and anhydrous ammonia may be combined under at least partially evacuated conditions. In still another embodiment, the propylene carbonate and the anhydrous ammonia may be combined in the presence of an initiator compound. In another embodiment, at least a portion of unreacted anhydrous ammonia may be removed to form hydroxypropyl carbamate product including greater than about 95% by weight of the hydroxypropyl carbamate. In another embodiment, at least a portion of unreacted anhydrous ammonia may be removed to form hydroxypropyl carbamate product including greater than about 97% by weight of the hydroxypropyl carbamate. In further embodiments, the propylene carbonate and the anhydrous ammonia may be combined at a temperature of greater than about 60° C., or alternatively at a temperature of greater than about 50° C.

In another respect the invention contemplates a process for preparing hydroxybutyl carbamate and a hydroxybutyl carbamate prepared by the process. The process includes combining butylene carbonate with anhydrous ammonia at a pressure of less than about 90 psig to form a reaction product including hydroxybutyl carbamate. In one embodiment of this process, the butylene carbonate may be combined with the anhydrous ammonia at a pressure of less than about 75 psig. In another embodiment, the butylene carbonate and the anhydrous ammonia may be combined under at least partially evacuated conditions. In still other embodiments of this process, the butylene carbonate and the anhydrous ammonia may be combined at a temperature of greater than about 60° C., or alternatively, at a temperature of greater than about 50° C. In a further embodiment, the butylene carbonate and the anhydrous ammonia may be combined in the presence of an initiator compound. In another embodiment, at least a portion of unreacted anhydrous ammonia may be removed to form hydroxybutyl carbamate product including greater than about 95% by weight of the hydroxybutyl carbamate. In yet another embodiment, at least a portion of unreacted anhydrous ammonia may be removed to form hydroxybutyl carbamate product including greater than about 97% by weight of the hydroxybutyl carbamate.

In another respect, the invention contemplates a process for preparing hydroxybutyl carbamate and a hydroxybutyl carbamate prepared by the process. The process includes combining butylene carbonate with anhydrous ammonia to form a reaction product including hydroxybutyl carbamate. In one embodiment of this process, the butylene carbonate may be 1,2-butylene carbonate, and the hydroxybutyl carbamate may be a mixture of 2-hydroxylbutyl carbamate and 1-hydroxymethyl propyl carbamate.

In another embodiment, the reaction product may include less than about 5% butylene glycol. In still other embodiments, at least a portion of unreacted anhydrous ammonia may be removed to form hydroxybutyl carbamate product including greater than about 95% by weight of the hydroxybutyl carbamate, or alternatively, to form hydroxybutyl carbamate product including greater than about 99% by weight of the hydroxybutyl carbamate. In a further embodiment of this process, the butylene carbonate and the anhydrous ammonia may be combined at a pressure of from about atmospheric to about 2000 psi. In other embodiments, the butylene carbonate and the anhydrous ammonia may be combined at a temperature of greater than about 60° C., or alternatively, at a temperature of greater than about 50° C. In a further embodiments, the hydroxybutyl carbamate prepared by this process may include from about 25% to about 75% of 2-hydroxylbutyl carbamate, and from about 75% to about 25% of 1-hydroxymethyl propyl carbamate. In a still further embodiment, the hydroxybutyl carbamate prepared by this process may include from about 40% to about 60% of 2-hydroxylbutyl carbamate, and from about 60% to about 40% of 1-hydroxymethyl propyl carbamate.

In another respect, the invention contemplates a composition that includes a mixture of 2-hydroxylbutyl carbamate and 1-hydroxymethyl propyl carbamate. In one embodiment, this composition may include from about 25% to about 75% of 2-hydroxylbutyl carbamate, and from about 75% to about 25% of 1-hydroxymethyl propyl carbamate. In another embodiment, this composition may include from about 40% to about 60% of 2-hydroxylbutyl carbamate, and from about 60% to about 40% of 1-hydroxymethyl propyl carbamate. In yet other embodiments, this composition may include greater than about 95% by weight hydroxybutyl carbamate, or alternatively, greater than about 99% by weight hydroxybutyl carbamate.

In another respect, this invention contemplates a composition including 2-hydroxylbutyl carbamate.

In another respect, this invention contemplates a composition including 1-hydroxymethyl propyl carbamate.

DESCRIPTION OF ILLUSTRATIVE EMBODIMENTS

In embodiments of the disclosed method high purity hydroxyalkyl carbamates may be produced by reacting alkyl carbamates and anhydrous ammonia in a conventional low pressure kettle. By "high purity" it is meant that a hydroxyalkyl carbamate product containing greater than about 95% hydroxyalkyl carbamate is achieved. Although the disclosed method is typically employed to produce high purity hydroxyalkyl carbamates, it will be understood with benefit of the present disclosure that it may also be employed to produce hydroxyalkyl carbamate products containing less than about 95% hydroxyalkyl carbamate.

Surprisingly, the disclosed method may be employed to produce high purity hydroxyalkyl carbamates having alkyl constituent groups with greater than two carbon atoms. Advantageously, the disclosed method may be employed to produce a high quality product using simple reaction procedures and equipment. This surprising result is achieved by the use of reactor vessel evacuation procedures and an initiator that allow reaction between alkylene carbonates and anhydrous ammonia to occur at relatively low pressures. Consequently, the disclosed method provides a relatively low cost, commercial batch process for producing hydroxyalkyl carbamates, such as hydroxypropyl and hydroxybutyl carbamates. The hydroxyalkyl carbamate product of this reaction typically does not require isolation by distillation or the like from an aqueous reaction product.

In the practice of the disclosed method, hydroxyalkyl carbamate compounds of the formula:

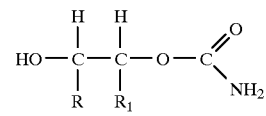

are typically produced, in which R and $R^1$ are hydrogen or an alkyl, in which R and $R^1$ may be the same or different, and in which at least one of R or $R^1$ is an alkyl. Typical examples include, but are not limited to, hydroxypropyl carbamates such as 2-hydroxy-2-methylethyl carbamate (2-hydroxypropyl carbamate) or 2-hydroxy-1-methylethyl carbamate; hydroxybutyl carbamates such as 2-hydroxylbutyl carbamate (or 1,2-butanediol 1-carbamate), 1-hydroxymethyl propyl carbamate (or 1,2-butanediol 2-carbamate), and mixtures thereof. In a most typical embodiment, a hydroxyalkyl carbamate is hydroxylpropyl carbamate. In another most typical embodiment, a hydroxyalkyl carbamate is hydroxylbutyl carbamate. Mixtures of two or more different carbamates, such as mixtures of hydroxypropyl and hydroxybutyl carbamates are also typical, as are mixtures of carbamate isomers of a single carbamate, such as a hydroxybutyl carbamate product comprising a mixture of 2-hydroxylbutyl carbamate and 1-hydroxymethyl propyl carbamate isomers.

Alkylene carbonates suitable for forming hydroxyalkyl carbamates of the disclosed method typically include those carbonates of the following structural formula:

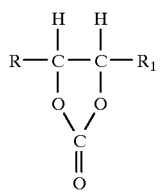

in which R and $R^1$ are hydrogen or alkyl, in which R and $R^1$ may be the same or different, and in which at least one of R or $R^1$ is an alkyl. Examples of suitable carbonates include, but are not limited to, propylene carbonate, butylene carbonate such as 1,2-butylene carbonate, 2,3-butylene carbonate, or isobutylene carbonate, and mixtures thereof. In this regard, it will be understood with benefit of the present disclosure that mixtures of alkylene carbonates and/or alkylene carbonate isomers may be employed to achieve products comprising mixtures of hydroxyalkyl carbamates and/ or mixtures of hydroxyalkyl carbamate isomers.

Although alkylene carbonates having three or more carbon atoms are typically reacted to form hydroxyalkyl carbamates as described above, it will be understood with benefit of the present disclosure that ethylene carbonate may also be reacted with anhydrous ammonia to form hydroxyethyl carbamate according to the methods described herein. Further, it will be understood that mixtures of ethylene carbonate and one or more alkylene carbonates having three or more carbon atoms may be reacted with anhydrous ammonia to form hydroxy alkyl carbamate mixtures having any desired percentage of hydroxyethyl carbamate mixed with a desired percentage/s of other hydroxy alkyl carbamate/s such as, for example, a mixture of 60% hydroxyethyl carbamate and 40% hydroxypropyl carbamate.

Advantageously, the disclosed method may be carried out at pressures within the operating pressure ranges of conventional kettles. Such maximum operating ranges are typically from about 75 to about 90 psig for batch kettles of various sizes, including those rated to an absolute maximum pressure of from about 100 to about 125 psi. Surprisingly then, high purity hydroxyalkyl carbamates may be produced in conventional low pressure kettles without exceeding the pressure rating of the kettles. This result is achieved by evacuating the reaction vessel, typically prior to the addition of anhydrous ammonia, and by using an initiator which serves to initiate the reaction of ammonia with alkylene carbonate in the absence of water. If a reaction vessel is not evacuated prior to the reaction, pressures may reach as high as 150 to 250 psig before reaction starts, making it unsafe to run the reaction in a conventional kettle. In addition, without initiator a reaction may not begin at pressures below the typical conventional kettle operating pressure limit of from about 75 to about 90 psig.

Initiator compounds may include any compounds suitable for reaction initiation. Examples of suitable initiators include hydroxyalkyl carbamates (such as the desired product of a reaction), glycol ethers and alcohols, or mixtures thereof. Typical alcohols include, but are not limited to, methyl alcohol, ethyl alcohol, etc. Any amount of initiator greater than about 0% by weight of alkylene carbonate and sufficient for initiating reaction between alkylene carbonate and anhydrous ammonia within the operating limits of a low pressure reaction vessel may be employed. In one embodiment, an initiator is typically present in an amount of greater than about 5%, and more typically greater than or equal to about 10%, by weight of alkylene carbonate. In another embodiment, an initiator is present in an amount of less than or equal to about 30%. In other embodiments, an initiator is present in an amount of from greater than about 5% to about 30%, more typically from greater than about 5% to about 25%, and most typically from about 10% to about 20% by weight of alkylene carbamate. An initiator is typically selected to be the same hydroxyalkyl carbamate as the product of the desired reaction such as, for example, a portion of the product from a previous reaction run. This eliminates the necessity of an extra process step to separate an initiator compound from the hydroxyalkyl carbamate product, such as may be required when an alcohol or other initiator compound is used.

In the practice of the disclosed method, alkylene glycols may be byproduct contaminants of the reaction, but are typically present in amounts of less than about 4%, more typically in amounts less than about 3%, and most typically in amounts less than about 2%. However, alkylene glycols may also be present in amounts greater than about 4% and in amounts less than about 1%. Because alkylene glycols may be formed by hydrolysis of alkylene carbonate starting materials in the presence of water, anhydrous ammonia is employed in the reaction. An excess of anhydrous ammonia is typically used to carry the reaction to completion and to reduce the concentration of free alkylene carbonate to a minimum, although no molar excess is required. Although any molar amount of anhydrous ammonia suitable for achieving a high purity hydroxyalkyl carbamate may be employed in the disclosed method, including between about 0% molar excess and about 5% molar excess, a molar excess of greater than about 5% anhydrous ammonia, more typically greater than or equal to about 10% anhydrous ammonia over the theoretical molar requirement for reaction with alkylene carbonate to form hydroxyalkyl carbamate is typically used. Even more typically, a molar excess of anhydrous ammonia is from about 10% to about 75%, more typically from about 10% to about 50%, and most typically from about 10% to about 25%. Although any anhydrous ammonia suitable for forming hydroxyalkyl carbamates of desired purity may employed in the disclosed method, typically an anhydrous ammonia having less than or equal to about 0.5% water content, more typically less than or equal to about 0.i% water con tent, is employ ed .

In the practice of the disclosed method, alkylene carbonate and anhydrous ammonia may be combined to form high purity hydroxyalkyl carbamate products using any suitable commercial or laboratory reaction equipment and/or processes known in the art. Examples of suitable reaction systems include, but are not limited to, kettles or autoclaves. Typically a conventional low pressure kettle is employed. Examples of such conventional low pressure kettles include, but are not limited to, alkoxylation type kettles available from Pfaudler, Autoclave Engineers, etc.

In one embodiment of the disclosed method, hydroxyalkyl carbamate is manufactured in a batch reaction using a reaction vessel, such as a conventional low pressure kettle. Prior to adding reactants, the vessel is typically at least partially evacuated, typically to a vacuum of from about 0.1 mm Hg to about 50 mm Hg, more typically to a vacuum of from about 1 mm Hg to about 30 mm Hg. The vessel is then charged with alkylene carbonate and initiator. Prior to the addition of ammonia, the vessel is then typically evacuated again in the same manner as described above. Evacuating the vessel twice, both before and after addition of alkylene carbonate and initiator, helps to ensure that the reactant carbonate and initiator are thoroughly degassed and that the initial pressure before ammonia addition is started is as low as possible. Although two separate evacuation steps are described above, it will be understood with benefit of the present disclosure that only one, or more than two, evacuation steps may be performed in conjunction with reaction of an alkylene carbonate and anhydrous ammonia according to the disclosed method. In addition, it will also be understood that any suitable manner of at least partially evacuating a reactor chamber may be employed so that the maximum reaction pressure, during ammonia addition and reaction, does not exceed the maximum operating pressure rating of a reaction vessel. In this embodiment, a reaction vessel is typically sealed following ammonia addition.

Prior to the addition of anhydrous ammonia, the reaction vessel containing alkylene carbonate and initiator may optionally be preheated, typically to a temperature that depends on the reaction temperature of the particular alkylene carbonate reactant or reactants. For example, in the case of propylene carbonate the vessel is typically preheated to a temperature of between about 35° C. and about 55° C., most typically between greater than about 50° C. and about 55° C. For butylene carbonate, the vessel is typically preheated to a temperature of between about 35° C. and about 65° C., most typically between about 60° C. and about 65° C. However, it will be understood with benefit of this disclosure that preheating is not necessary. Anhydrous ammonia is then typically added to the reaction vessel in a molar excess as described above. Typically, ammonia is added slowly so that the reactor pressure does not exceed the pressure limitations of the vessel. In this regard, the pressure typically does not exceed about 75 psig, even more typically does not exceed about 70 psig, even more typically does not exceed about 60 psig, and most typically does not exceed about 55 psig. In one embodiment, for example, ammonia addition is typically accomplished over a time period of from about 0.5 to about 3 hours, more typically over a time period of from about I to about 2 hours. However, it will be understood that ammonia addition times of less than about 0.5 hours and greater than about 3 hours are also possible.

Although the disclosed method is typically carried out at pressures that do not exceed the pressure limitations of the reactor vessel, it will be understood with benefit of the present disclosure that the disclosed method may otherwise be carried out at any reactor pressure suitable for forming hydroxyalkyl carbamate, including pressures greater than about 75 psig.

After addition of ammonia the reaction mixture is typically maintained at a reaction temperature for a digestion time selected to allow sufficient alkylene carbonate to be converted to hydroxyalkyl carbamate for the desired purity requirement. Any reaction temperature suitable for production of high purity hydroxyalkyl carbamate may be employed. However, with benefit of this disclosure, it will be understood that reaction temperatures and digestion times may depend on the particular alkylene carbonate reactant selected and/or on the purity of product desired. For example to produce a hydroxypropyl carbamate product having a purity of greater than about 95%, the reaction is allowed to proceed until less than about 2% propylene carbonate remains. Longer reaction times will typically result in decreased purity due to increased production of alkylene glycols (in this case propylene glycol). A specific reaction time to get to this concentration of propylene carbonate will depend on reaction temperature. For example, a hydroxypropyl carbamate reaction carried out at from about 75° C. to about 85° C. will typically reach this point after about 1 to about 3 hours. By varying the temperature, the reaction time to achieve a desired purity may be controlled.

It will be understood with benefit of the present disclosure that reaction time and product purity typically decrease with increasing temperature. Accordingly, in one embodiment, a propylene carbonate/anhydrous ammonia mixture is typically allowed to react or digest at temperatures of less than about 85° C., as product purity may decrease with increasing temperatures. In another embodiment, the reaction temperature is kept above about 60° C., as reaction time tends to decrease with increasing temperatures and high purity levels may not be achieved in commercially reasonable reaction times. In still another embodiment, the reaction temperature may be kept between greater than about 60° C. and less than or equal to about 85° C. In yet another embodiment, the reaction temperature is kept greater than about 50° C.

However, other propylene carbonate/anhydrous ammonia reaction temperature embodiments are possible. For example, a propylene carbonate/anhydrous ammonia mixture may be allowed to react or digest at a temperature of from about 40° C. to about 120° C., more typically from greater than about 50° C. to about 100° C., even more typically from about 55° C. to about 100° C., even more typically from about 60° C. to about 95° C., even more typically from about 70° C. to about 90° C., even more typically from about 70° C. to about 85° C., and most typically from about 80° C. to about 85° C. Digestion times for a propylene carbonate/anhydrous ammonia mixture is typically between about 1 hour and about 6 hours, more typically between about 1.5 hours and about 5 hours, and most typically between about 2 hours and about 4 hours.

Similarly, multiple temperature embodiments are possible in the production of hydroxybutyl carbamate. For example, a butylene carbonate/anhydrous ammonia mixture is typically allowed to react or digest at temperatures of less than about 85° C. In another embodiment, the reaction temperature is kept above about 60° C. In still another embodiment, the reaction temperature may be kept between greater than about 60° C. and less than or equal to about 85° C. In yet another embodiment, the reaction temperature is kept greater than about 50° C.

However, other butylene carbonate/anhydrous ammonia reaction temperature embodiments are possible. For example, a butylene carbonate/anhydrous ammonia mixture may be allowed to react or digest at a temperature of between about 40° C. and about 120° C., more typically between greater than about 50° C. and about 100° C., even more typically from about 55° C. to about 100° C., even more typically from about 60° C. to about 95° C., even more typically between about 70° C. and about 90° C., even more typically between about 70° C. and about 88° C., and most typically between about 80° C. and about 85° C. Digestion time for a butylene carbonate/anhydrous ammonia mixture is typically from about 1 hour to about 8 hours, more typically from about 1.5 hours to about 7 hours, and most typically from about 2 hours to about 6 hours.

In other embodiments involving the production of hydroxyethyl carbamate or hydroxyethyl/hydroxypropyl carbamate mixtures, an ethylene carbonate/anhydrous ammonia mixture or mixture of ethylene carbonate, propylene carbonate and anhydrous ammonia is typically maintained at a reaction temperature of less than about 60° C. More typically such mixtures are reacted at a temperature greater than about 50° C. and less than or equal to about 60° C. However, temperatures greater than about 60° C. are also possible. Such mixtures are typically digested for a period of about 1 hour to about 3 hours, more typically from about 1.5 hours to about 2 hours. Relatively longer digestion times (greater than about 3 hours) and greater amounts of initiator and ammonia are typically employed in the production of hydroxyethyl/hydroxypropyl carbamate.

During the digestion period, the reaction pressure typically decreases. Maximum reaction pressure during ammonia addition and reaction may be controlled by the rate at which anhydrous ammonia is added. In this regard, any maximum reaction pressure suitable for production of high purity hydroxyalkyl carbamates may be employed. However, with benefit of this disclosure, it will be understood that maximum reaction pressure may depend on the particular alkylene carbonate reactant selected and/or the pressure rating of the reaction equipment employed. In this regard, in one embodiment of the disclosed method maximum reaction pressures are generally kept less than about 90 psig and may be as low as subatmospheric. More typically, maximum reaction pressures are kept below about 75 psig, and most typically below about 70 psig. However, other maximum reaction pressure embodiments are possible. For example, in other embodiments, maximum reaction pressures may be between about 35 psig and about 75 psi, more typically between about 40 psig and about 75 psi, even more typically between about 40 psig and about 70 psi, and most typically between about 45 psig and about 65 psi. Following a typical reaction between propylene carbonate and anhydrous ammonia, concentration of unreacted propylene carbonate is typically less than about 4%, more typically less than about 3% and most typically less than about 2%. Following a typical reaction between butylene carbonate and anhydrous ammonia, concentration of unreacted butylene carbonate is typically less than about 5%, more typically less than about 4%, and most typically less than about 3%.

For ethylene carbonate/anhydrous ammonia and ethylene carbonate/propylene carbonate/anhydrous ammonia mixtures, maximum reaction pressure is typically kept at about 55 psig or less, more typically at about 45 psig or less, and most typically at about 35 psig or less. Following reaction, concentration of unreacted carbonate is typically less than about 1%, and most typically less than or equal to about 0.5%.

Following reaction, excess ammonia may be removed from a hydroxyalkyl carbamate product using any suitable method known in the art. Typically, at least a portion of any excess unreacted ammonia is removed by vacuum stripping, for example, by using a steam jet or vacuum pump. Typically, vacuum stripping is carried out at a temperature of from about 50° C. to about 80° C. and a vacuum of from about 1 mm Hg to about 50 mm Hg for a time period of from about 1 to about 24 hours. Alternatively, gas stripping with, for example nitrogen, may also be employed to remove excess ammonia alone, or in combination, with vacuum stripping.

Following removal of excess ammonia, a typical hydroxypropyl carbamate product produced according to the above method has a purity of greater than about 95%, more typically greater than about 96% and most typically greater than about 97%, although purity levels less than or equal to about 95% are also possible. A typical hydroxypropyl carbamate product typically includes two isomers, 2-hydroxy-2-methylethyl carbamate and 2-hydroxy-1-methylethyl carbamate. These isomers are typically present in substantially equal quantities. Such a hydroxypropyl carbamate product typically includes less than about 2.5% propylene glycol and less than about 2.5% unreacted propylene carbonate, although greater amounts of either or both are also possible.

Following removal of excess ammonia, a typical hydroxybutyl carbamate product produced according to the above method has a purity of greater than about 95%, more typically greater than about 96% and most typically greater than about 97%, although purity levels less than or equal to about 95% are also possible. A typical hydroxybutyl carbamate product typically includes two isomers, 2-hydroxybutyl carbamate and 1-hydroxymethyl propyl carbamate. These isomers are typically present in substantially equal quantities. Such a hydroxybutyl carbamate product typically includes less than about 2.5% butylene glycol and less than about 2.5% unreacted butylene carbonate, although greater amounts of either or both are also possible.

Following removal of excess ammonia, a typical hydroxyethyl carbamate product produced according to the above method has a purity of greater than about 95%, more typically greater than about 96% and most typically greater than about 97%, although purity levels less than or equal to about 95% are also possible. Such a hydroxyethyl carbamate product typically includes less than about 2.5% ethylene glycol and less than about 2.5% unreacted ethylene carbonate, although greater amounts of either or both are also possible.

In one most typical embodiment of the disclosed method for the production of hydroxypropyl carbamate, propylene carbonate is reacted with greater than or equal to about 10% excess anhydrous ammonia in the presence of about 10% to about 20% hydroxypropyl carbamate initiator in an evacuated low pressure kettle. Reaction temperature is typically from about 70° C. and about 85° C. and maximum reaction pressure typically between about 40 psig and about 75 psig.

In one most typical embodiment of the disclosed method for the production of hydroxybutyl carbamate, butylene carbonate is reacted with greater than or equal to about 10% excess anhydrous ammonia in the presence of about 5% to about 25% hydroxybutyl carbamate initiator in an evacuated low pressure kettle. Reaction temperature is typically from greater than about 50° C. to about 100° C. and maximum reaction pressure typically between about 35 psi, and about 75 psig.

In one most typical embodiment for the production of hydroxyethyl carbamate, ethylene carbonate is reacted with greater than or equal to about 10% excess anhydrous ammonia in the presence of about 5% to about 25% hydroxyethyl carbamate initiator in an evacuated low pressure kettle. Reaction temperature is typically from greater than about 50° C. to about 80° C. and maximum reaction pressure is typically between about 30 psig and about 75 psig.

In one most typical embodiment for the production of hydroxyethyl/hydroxypropyl carbamate, a mixture of 60% ethylene carbonate and 40% propylene carbonate is reacted with greater than or equal to about 10% excess anhydrous ammonia in the presence of about 5% to about 25% of a mixture of about 60% ethylene carbonate and about 40% propylene carbonate initiator in an evacuated low pressure kettle. Reaction temperature is typically from greater than about 50° C. to about 80° C., and maximum reaction pressure is typically between about 30 psig and about 75 psig.

Hydroxyalkyl Carbamate Compositions

Isomers and mixtures of isomers of hydroxyalkyl carbamates and mixtures of hydroxyalkyl carbamates as described herein may be made from the reaction of alkylene carbonates and mixtures of alkylene carbonates with anhydrous or aqueous ammonia under a variety of conditions, both in low pressure kettles as described previously, and under higher pressure conditions, for example at pressures equal to or greater than about 90 psig. Possible alkylene carbonates that may be reacted under these conditions include those alkylene carbonates having a total of three or more carbon atoms (such as ethylene carbonate), more typically having four or more carbon atoms (such as propylene carbonate), and most typically having a total of five or more carbon atoms (such as butylene carbonate).

Because aqueous ammonia or ammonium hydroxide typically results in the formation of greater amounts of alkylene glycol byproduct, anhydrous ammonia is typically employed in those cases where high purity hydroxyalkyl carbamate product is desired. However, aqueous ammonia such as, for example, a concentrated (30%) ammonium hydroxide solution, may be successfully employed where lower purity carbamate products are permissible.

In one embodiment of the disclosed method, 1,2-butylene carbonate may be reacted with anhydrous or aqueous ammonia under any reaction conditions suitable for producing a hydroxybutyl carbamate product comprising a mixture of two isomers: 2-hydroxylbutyl carbamate (or 1,2-butanediol 1-carbamate), and 1-hydroxymethyl propyl carbamate (or 1,2-butanediol 2-carbamate), formulas of which are shown below.

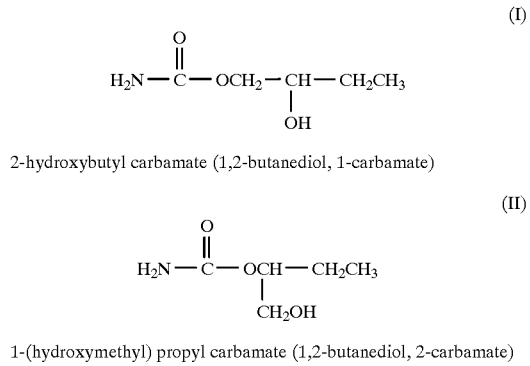

2-hydroxybutyl carbamate (1,2-butanediol, 1-carbamate)

1-(hydroxymethyl) propyl carbamate (1,2-butanediol, 2-carbamate)

Because aqueous ammonia typically results in the formation of greater amounts of alkylene glycol byproduct, e.g., typically about 5% glycol or more, anhydrous ammonia is typically employed in those cases where high purity butylene carbamate product is desired. Advantageously then, hydroxybutyl carbamate reaction products comprising a mixture of 2-hydroxylbutyl carbamate (or 1,2-butanediol 1-carbamate) and 1-hydroxymethyl propyl carbamate (or 1,2-butanediol 2-carbamate), and typically containing less than about 5% butylene glycol, more typically less than about 4% butylene glycol, even more typically less than about 3% butylene glycol, even more typically less than about 2% butylene glycol, and most typically less than about 1% butylene glycol may be produced by reacting 1,2-butylene carbonate with anhydrous ammonia. However, aqueous ammonia may be successfully employed where lower purity carbamate products are permissible.

In one embodiment of the disclosed method, butylene carbonate may be reacted with anhydrous or aqueous ammonia in any reactor or reaction vessel suitable for producing the two hydroxybutyl carbamate isomers described above. Reactions employing low pressure kettle reactors have been described previously. Other examples of suitable reactor types include, but are not limited to, stirred reactors, continuously stirred reactors, tubular reactors, etc. As described previously, an initiator and vessel evacuation are typically employed when reactions are performed within a low pressure reactor vessel, e.g., vessels having maximum operating pressure ranges of from about 75 psig to about 90 psig. However, reactions within higher pressure reaction vessels may be performed with or without initiator, and/or with or without evacuation.

In the practice of one embodiment of the disclosed method, 1,2-butylene carbonate may be reacted with anhydrous or aqueous ammonia under any conditions suitable for producing a hydroxybutyl carbamate product comprising 2-hydroxylbutyl carbamate (1,2-butanediol 1-carbamate), 1-hydroxymethyl propyl carbamate (1,2-butanediol 2-carbamate), or mixtures thereof. Typically, such reactions are carried out at a pressure of from about atmospheric to about 2000 psig, more typically from about 50 psig to about 1000 psig, and most typically from about 50 psig to about 500 psig. However, reaction pressures greater than about 2000 psig and less than about atmospheric may also be employed. Further, in one embodiment such reactions are typically carried out at a temperature of greater than about 50° C., and more typically greater than about 60° C. In other embodiments, such reactions are typically carried out at temperatures of from about 30° C. to about 200° C., more typically from about 50° C. to about 100° C., and most typically from about 60° C. to about 80° C. However, temperatures greater than about 200° C. and less than about 30° C. may also be employed.

Amounts of excess ammonia reactant employed in the production of hydroxybutyl carbamates in low pressure reaction vessels have been described above. However, it will be understood with benefit of the present disclosure that reactions carried out in reaction vessels with higher pressure ratings may utilize greater excesses of ammonia and achieve higher carbamate product purity levels. Typically from about 10% to about 300% molar excess of ammonia (in relation to butylene carbonate), more typically from about 10% to about 200% molar excess of ammonia, and most typically from about 10% to about 80% molar excess of ammonia is employed as a reactant. However, it will be understood with benefit of the present disclosure that any other amount of ammonia in relation to butylene carbonate suitable for reacting and forming hydroxybutyl carbamate may be employed including, but not limited to, no molar excess of ammonia, molar excesses less than 10%, and molar excesses greater than 300%. A product initiator as previously described is not required for higher pressure reactions (such as reactions occurring at above about 100 psig), but may be utilized to reduce the resonance time to complete the reaction.

It will be understood with benefit of the present disclosure that reaction times are typically dependent on reaction temperature. For example, in one embodiment complete reaction of 1,2 butylene carbonate with anhydrous ammonia typically occurs in about 10 hrs at about 50° C., in about 6 hours at about 60° C., in about 4 hours at about 70° C., and in about 1 hour at about 100° C. degrees. When aqueous ammonia is employed as a reactant, reaction rate is typically faster and time for complete reaction is typically shorter.

In a typical embodiment of the disclosed method, 1,2 butylene carbonate is reacted with anhydrous ammonia to yield a reaction product typically comprising a molar ratio of from about 25% to about 75% of 2-hydroxylbutyl carbamate (or 1,2-butanediol 1-carbamate), and from about 75% to about 25% of 1-hydroxymethyl propyl carbamate (or 1,2-butanediol 2-carbamate). More typically, such a reaction yields from about 70% to about 30% of 2-hydroxylbutyl carbamate (or 1,2-butanediol 1-carbamate), and from about 30% to about 70% of 1-hydroxymethyl propyl carbamate (or 1,2-butanediol 2-carbamate). Even more typically such a reaction yields from about 35% to about 65% of 2-hydroxylbutyl carbamate (or 1,2-butanediol 1-carbamate), and from about 65% to about 35% of 1-hydroxymethyl propyl carbamate (or 1,2-butanediol 2-carbamate), and most typically such a reaction yields from about 40% to about 60% of 2-hydroxylbutyl carbamate (or 1,2-butanediol 1-carbamate), and from about 60% to about 40% of 1-hydroxymethyl propyl carbamate (or 1,2-butanediol 2-carbamate). In this regard it will be understood with benefit of the present disclosure that greater percentages of the primary hydroxyl isomer will be generated with lower reaction temperatures, and that greater percentages of the secondary hydroxyl isomer will be generated at higher temperatures. Following reaction, excess ammonia may be removed from the reaction product using vacuum or gas stripping methods previously described herein as well as using any suitable method known in the art. Advantageously then, using the disclosed method, the above-described isomer mixtures may be produced at a purity level of typically greater than about 95%, even more typically greater than about 96%, even more typically greater than about 97%, even more typically greater than about 98%, and most typically greater than about 99%.

In another possible embodiment, propylene carbonate may be reacted with anhydrous ammonia to form hydroxypropyl carbamate, typically at a temperature of between about 50° C. and about 90° C, at a pressure between about 90 psig and about 350 psig (more typically at a pressure of between about 100 psig and about and about 350 psig), and for a reaction period of about 1 to about 5 hours.

EXAMPLES

The following examples are illustrative and should not be construed as limiting the scope of the invention or claims thereof.

Example 1

Production of Hydroxypropyl Carbamate with 20% Excess Ammonia

To a 1 liter 316 stainless steel autoclave was added 449.2 grams (4.4 moles) of propylene carbonate and 89.8 grams of hydroxypropyl carbamate made in a prior run. The amount of hydroxypropyl carbamate initiator employed was equivalent to 20% by weight basis of the propylene carbonate. The reactor containing the propylene carbonate and hydroxypropyl carbamate initiator was evacuated using a vacuum pump to maximum vacuum (25 inches Hg vac). The evacuated autoclave was heated to 45° C. and anhydrous ammonia was added slowly such that 90 g (5.3 moles) of ammonia was added over a 60 minute period. This was equivalent to about a 20% molar excess of anhydrous ammonia. The pressure rose to a maximum of 60 psig during the ammonia addition. After ammonia addition was complete, the reactor was heated to 85° C. and held at that temperature for 2 hours. During this digestion period, the pressure fell from 56 psig to 15 psig. The product was stripped of excess ammonia by placing it in a 1-liter round-bottomed flask and heating to 50–60° C. under maximum vacuum for 2.0 hours. The resulting hydroxypropyl carbamate product was 98.7% pure and contained two hydroxypropyl carbamate isomers, 2-hydroxy-2-methylethyl carbamate and 2-hydroxy-1-methyl ethyl carbamate in approximately equal quantities. The product also contained 0.7% propylene glycol and 0.6% propylene carbonate (unreacted). The OH number was 463 mg KOH/g.

Example 2

Production of Hydroxypropyl Carbamate with 15% Excess Ammonia

To a 1 liter autoclave was added 449.2 grams of propylene carbonate (4.4 moles) and 89.8 grams of hydroxypropyl carbamate made in a previous run. The amount of hydroxypropyl carbamate initiator employed was equivalent to 20% by weight basis of the propylene carbonate. The autoclave was evacuated to maximum vacuum (25 inches Hg vac) using a vacuum pump. The autoclave was heated to 44–45° C. and 86.0 grams (5.06 moles) of anhydrous ammonia was added slowly over a I hour period. This was equivalent to about a 15% molar excess of anhydrous ammonia. The maximum pressure developed during addition of the ammonia was 65 psig. After the ammonia addition was complete, the reaction mixture was heated to 85° C. and held at that temperature for 3 hours with stirring. The product was stripped of excess ammonia by placing it in a I liter round-bottomed flask and heating to 50–60° C. under full vacuum for 2 hours. The hydroxypropyl carbamate product was 98.4% pure and contained 2 isomers (about 50/50 by wt $^2$-hydroxy-2-methylethyl carbamate and 2-hydroxy-1-methylethyl carbamate) with 0.8% propylene glycol and 0.8% propylene carbonate (unreacted). The OH number of the stripped product was 468 mgKOH/g sample.

Example 3

Production of Hydroxypropyl Carbamate with 10% Excess Ammonia

To a 1 liter autoclave was added 449.2 gram of propylene carbonate (4.4 moles) and 89.8 grams of hydroxypropyl carbamate (made in previous run). The amount of hydroxypropyl carbamate initiator was equivalent to 20% weight basis of the propylene carbonate. The autoclave was evacuated to maximum vacuum (25 Hg vac) using a vacuum pump. The autoclave was heated to 45° C. Once at that temperature, the addition of anhydrous ammonia was begun and continued over a one hour period, during which 82.3 grams (4.84 moles) of $NH_3$ were added. The maximum pressure reached during the addition of ammonia was 59 psig, well under the 75–90 psig limit of most conventional kettles. After the addition of the ammonia was complete, the reaction mixture was heated at 85° C. for 4.0 hours. The pressure fell from 52 to 10 psig. The excess ammonia was stripped as described in Examples 1 and 2. The hydroxypropyl carbamate reaction product was 98.4% pure, containing two isomers (about 50/50 by weight 2-hydroxy-2-methylethyl carbamate and 2-hydroxy-1-methylethyl carbamate) and 0.9% propylene glycol and 0.7% propylene carbonate.

Example 4

Production of Hydroxypropyl Carbamate with 5% Initiator

The procedure of Examples 1–3 was repeated except only 5% product initiator was employed. In this example the reaction pressure reached 113 psig. The results of this example indicate the importance that sufficient initiator be employed to maintain the reaction pressure low.

Example 5

Production of Hydroxypropyl Carbamate Without Initiator

The procedures of Example 1–3 was repeated using no initiator. In this experiment the reaction pressure 146 psig. Like Example 4, the results of this example indicate the importance of an initiator in maintaining the reaction pressure low.

Example 6

Production of Hydroxypropyl Carbamate Without Reactor Evacuation

The following example was performed using hydroxypropyl carbamate product initiator at 85° C. for 2 hours. To a one-gallon autoclave was added 2246.0 grams (22 moles) propylene carbonate and 112.3 grams of hydroxypropyl carbamate initiator. The initiator was present in an amount equivalent to 5% by weight basis of propylene carbonate. To this mixture at 23° C. was added 468 g (27.5 moles) anhydrous ammonia. This was about 25% molar excess of ammonia. The autoclave was heated slowly to 85° C. at the end of the reaction. The maximum pressure reached 140 psig before reaction started and pressure dropped to 48 psig at 85° C. at the end of the reaction. After stripping excess ammonia as described previously, the hydroxypropyl carbamate reaction product contained 0.7% propylene glycol, 0.4% propylene carbamate and 98.9% hydroxypropyl carbamate. The maximum pressure reached during the addition of the ammonia and heating to reaction temperature (before the ammonia reacted away) was 140 psig, too high for a conventional kettle.

The results of examples 4 through 6 show the importance of both reactor evacuation and the presence of an initiator such as hydroxypropyl carbamate product in the successful production of hydroxypropyl carbamate in a conventional low pressure kettle (typically having a maximum operating pressure of less than about 75 psig to about 90 psig).

Example 7

Production of Hydroxybutyl Carbamate with 20% Initiator and 30% Excess Ammonia 1,2-Butylene carbonate (99.9% purity, 1975.4 grams, 17.0 moles) was premixed with hydroxybutyl carbamate (395.0 grams, 20% basis amount of 1,2-butylene carbonate) and the liquids added to a clean, dry, 1-gallon 316 stainless steel, stirred autoclave. The clave was evacuated with a vacuum pump to achieve −28 psig vacuum (maximum vacuum). Anhydrous ammonia was added slowly at 55–60° C. so the pressure of the reaction never exceeded 75 psig (thus enabling this reaction to be done, for example, in a conventional kettle rated at 100–125 psig). A total of 374.0 grams of anhydrous ammonia was added (22.0 moles) over a two hour period at 55–60° C. After the ammonia addition was complete, the reaction mixture was stirred at 60° C. for 6.0 hours. The pressure fell from 70 psig to 4 psig. The crude product was stripped at 3 mmHg at 70° C. for 16 hours. The resulting reaction mixture was analyzed by gas chromatography and found to contain 96.9% hydroxybutyl carbamate, 0.9% 1,2-butylene glycol, and 2.2% 1,2-butylene carbonate. The hydroxybutyl carbamate was a mixture of two isomers: 53.1% 1,2-butanediol, 1-carbamate, and 43.8% 1,2-butanediol, 2-carbamate.

Example 8

Production of Hydroxyethyl Carbamate with 10% Initiator and 20% Excess Ammonia In one typical embodiment for producing hydroxyethyl carbamate, an evacuated reaction vessel is charged with ethylene carbonate and about 10% hydroxyethyl carbamate initiator. This charge mixture is preheated to about 50° C. and ammonia addition started. In this embodiment, reaction temperature is maintained at about 55° C. during ammonia addition, and a maximum pressure of about 35 psig is typically attained during the reaction. Pressure is typically allowed to become constant during digestion and may be subatmospheric. After addition of the required ammonia charge, which typically includes a 20% excess over the theoretical, the reaction is digested for about 1.5 hours at about 60° C. Following digestion, additional ammonia may be fed to the reactor and digested if free carbonate content is greater than desired. For example, if free carbonate is greater than about 0.5%, an additional 5% ammonia may be added and digested for about 30 minutes. In this embodiment, excess ammonia may be removed (such as to about 0.15% or less) by vacuum stripping, first at about 60° C. to an absolute pressure of 100 mm Hg, and then at 70° C. to a final pressure of about 10 mm Hg. It will be understood with benefit of this disclosure that gas stripping with nitrogen or other suitable gas may also be used to remove excess ammonia in conjunction with vacuum stripping or as a replacement for vacuum stripping, such as where sufficient vacuum is not attainable.

Table I summarizes data for a hydroxyethyl carbamate production run.

TABLE 1

Summary of Charge Weights and Process Conditions

| Reactor Charge, Lb. | |
|---|---|
| (Basis: 1000 gal. kettle) | |
| Hydroxyethyl carbamate | 665 |
| Ethylene carbonate | 6650 |
| Ammonia | 1542 |
| Product Yield, Lb. | 8365 |
| % of Theoretical | 97 |
| Process Conditions | |
| Start ammonia addition: | |
| Temp., ° C. | 50 |
| Pressure, psig | Evacuated kettle |
| Reaction: | |
| Temp, ° C. | 55 |
| Pressure, psig, max. | ~35 |
| Digestion: | |
| Temp, ° C. | 60 |
| Pressure, psig | To constant pressure |
| Vacuum Stripping:* | |
| (a) Temp., ° C. | 60 |
| Pressure, mm Hg | 100 |
| (b) Temp., ° C. | 70 |
| Pressure, mm Hg | 10 |
| Discharge to storage: | |
| Temp., ° C. | 60 |
| Cycle Time, Hrs. | |
| (Basis: 300 gal. kettle) | |
| Charge and initial warm-up | 1.25 |
| Reaction with ammonia | 1.50 |
| Digestion | 1.50 |
| Ammonia stripping* | 1.50 |
| Cool and transfer | 1.00 |
| Total | 6.75 |

*Based on vacuum stripping

Example 9

Production of Hydroxyethyl/hydroxypropyl Carbamate With 15% Initiator and 30% Excess Ammonia In another embodiment, hydroxyethyl/hydroxypropyl carbamate may be manufactured using a similar procedure as given in Example 8 for hydroxyethyl carbamate, however a mixture of hydroxyethyl and hydroxypropyl carbamate is typically employed as an initiator, and a mixture of ethylene and propylene carbonate reactants is initially charged to the reactor. In this regard, the initial reactor charge typically includes about 15% initiator and a 30% excess of ammonia is used. Typical digestion time is about two hours at about 60° C.

Table 2 summarizes data for a hydroxyethyl/hydroxypropyl carbamate production run.

TABLE 2

Summary of Charge Weights and Process Conditions

Reactor Charge, Lb.

(Basis: 1000 gal. kettle)

| | |
|---|---|
| Hydroxyethyl/Hydroxypropyl Carbamate | 937 |
| Ethylene carbonate | 3750 |
| Propylene carbonate | 2500 |
| Ammonia | 1482 |
| Product Yield, Lb. | 8090 |
| % of Theoretical | 97 |

Process Conditions

Start ammonia addition:

| | |
|---|---|
| Temp., ° C. | 50 |
| Pressure, psig | Evacuated kettle |

Reaction:

| | |
|---|---|
| Temp, ° C. | 55 |
| Pressure, psig, max. | 35 |

Digestion:

| | |
|---|---|
| Temp, ° C. | 60 |
| Pressure, psig | To constant pressure |

Vacuum Stripping:*

| | |
|---|---|
| (a) Temp., ° C. | 60 |
| Pressure, mm Hg | 100 |
| (b) Temp., ° C. | 70 |
| Pressure, mm Hg | 10 |

Discharge to storage:

| | |
|---|---|
| Temp., ° C. | 38 |

Cycle Time, Hrs.

(Basis: 300 gal. kettle)

| | |
|---|---|
| Charge and initial warm-up | 1.25 |
| Reaction with ammonia | 1.50 |
| Digestion | 2.00 |
| Ammonia stripping* | 1.50 |
| Cool and transfer | 1.50 |
| Total | 7.75 |

*Based on vacuum stripping

Example 10

Higher Pressure Production of Hydroxybutyl Carbamate with 50% Excess Anhydrous Ammonia 1,2-Butylene carbonate (99.9% purity, 1975.4 grams, 17.0 moles) was added to a clean, dry, 1-gallon, 316 stainless steel, stirred autoclave. The clave was sealed and the clave and contents were heated to 55° C. At 55° C., anhydrous ammonia (433.5 grams, 25.5 moles) was added over a 50–60 minute period with the reaction temperature between 55–60° C. After the addition of ammonia was complete, the reaction mixture was stirred and kept at 60° C. for 6.0 hours. The maximum pressure reached 235 psi. The crude product was stripped at 1 to 3 mmHg for 12 hours at 75° C. Gas chromatography indicated the product was 99.1% hydroxybutyl carbonate (2 isomers), 0.6% 1,2-butylene glycol, and 0.3% 1,2-butylene carbonate. NMR indicated that 2 isomers were present in the following molar ratio: 45.8% of (2-hydroxybutyl carbamate (1,2-butanediol, 1-carbamate)) 1,2-butanediol, 1-carbamate (or 2-hydroxybutyl carbamate) and 54.2% of (1-(hydroxymethyl) propyl carbamate (1,2-butanediol, 2-carbamate)) 1,2-butanediol, 2-carbamate (or 1-(hydroxymethyl) propyl carbamate).

Example 11

Higher Pressure Production of Hydroxybutyl Carbamate with 50% Excess Anhydrous Ammonia In this Example, an experiment identical to Example 10 was performed, except that the reaction was conducted at 70° C. for 4 hours (after ammonia addition complete). The crude product was stripped at 1 to 3 mmHg for 7 hours at 70° C. GLC analysis indicated a reaction product comprising 98.4% hydroxybutyl carbamate, 1.1% 1,2-butylene glycol, and 0.5% 1,2-butylene carbonate. NMR indicated isomers having a molar ratio of 58.0% (2-hydroxybutyl carbamate (1,2-butanediol, 1-carbamate)) and 42% (1-(hydroxymethyl) propyl carbamate (1,2-butanediol, 2-carbamate)). In this example, the maximum reaction pressure reached 265 psig.

Additional Examples A–G

Production of Hydroxypropyl Carbamate

The following examples were performed using a 1 liter 316 stainless steel autoclave to which propylene carbonate and ammonia were added in the molar amounts shown in Table 3. As indicated in Table 3, aqueous ammonia was added to propylene carbonate without initiator in Examples C–G. In Examples A and B, anhydrous ammonia was added to propylene carbonate without and with initiator, respectively. No autoclave evacuation procedures were employed in any of Examples A–G.

In each of Examples A and B, reaction temperature was held at 50° C. throughout a three hour reaction run. Example B (with initiator) produced a hydroxypropyl carbamate reaction product containing 99.3% hydroxypropyl carbamate and Example A (without initiator) produced a reaction product containing 96.0% hydroxypropyl carbamate. However, in each case reaction pressure exceeded 100 psig, particularly in Example A in the absence of initiator. The results of Examples A and B further illustrate the importance of both reactor evacuation and the presence of an initiator in the successful production of hydroxyalkyl carbamates in a conventional low pressure kettle.

In each of Examples C–G, similar amounts of propylene carbonate and aqueous ammonia were employed without initiator. In each case, aqueous ammonia was added to propylene carbonate at a temperature of 30° C. In Examples C–E, reaction temperature was maintained at 30° C. for reaction run times of 3, 6 and 24 hours, respectively. Although maximum reaction pressures were below 50 psig in each case, the purity of hydroxypropyl carbamate reaction product in each case was well below 95%. As can be seen in Table 3, the concentration of hydroxypropyl carbamate in the reaction product tended to decrease, and the concentration of propylene glycol increase, with increasing reaction time. The results of Examples C–E demonstrate that reactions between alkylene carbonate and aqueous ammonia tend to produce hydroxyalkyl carbamate reaction products having purity levels of less than 90%.

In Examples F and G, the procedure of Examples C–E was repeated except that reaction temperatures of 50° C. and 85° C., respectively, were employed. In these examples, purity of hydroxypropyl carbamate reaction product was further reduced in comparison to Examples C–E. Furthermore, in Example G the maximum reaction pressure was 178 psig, considerably higher than in the other examples.

TABLE 3

| Example | Propylene Carbonate (PC), (moles) | *Hydroxypropyl Carbamate (HPC) Initiator (if used) | Anhydrous Ammonia (moles) | Aqueous Ammonia (moles) | Temp Ammonia Added (° C.) | Max. Press (psig) | Run Temp (° C.) | Run Time (Hrs) | GLC Analysis (%) | | |
|---|---|---|---|---|---|---|---|---|---|---|---|
| | | | | | | | | | HPC | PC | Propylene Glycol |
| A | 4.0 | No | 4.8 | — | 50 | 140 | 50 | 3.0 | 96.0 | 3.7 | 0.3 |
| B | 4.0 | Yes | 4.8 | — | 50 | 102 | 50 | 3.0 | 99.3 | — | 0.4 |
| C | 3.0 | No | — | 3.6 | 30 | 45 | 30 | 3.0 | 83.0 | 10.4 | 6.6 |
| D | 3.0 | No | — | 3.6 | 30 | 47 | 30 | 6.0 | 82.8 | 10.2 | 7.0 |
| E | 3.0 | No | — | 3.6 | 30 | 30 | 30 | 24.0 | 74.5 | 5.5 | 20.0 |
| F | 3.0 | No | — | 3.6 | 30 | 38 | 50 | 3.0 | 71.4 | 5.1 | 23.5 |
| G | 3.0 | No | — | 3.6 | 30 | 178 | 85 | 2.0 | 66.7 | 3.6 | 29.7 |

*Hydroxypropyl Carbamate initiator present in an amount equivalent to 20% by weight of propylene carbonate.

Those skilled in the art will understand with benefit of the present disclosure that the disclosed ranges of pressure, temperature, reactant concentrations and initiator concentrations may be varied and applied in different combinations in order to achieve hydroxyalkyl carbamate reaction products having desired purities, within desired reaction times and pressure constraints.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed compositions and methods may be utilized in various combinations and/or independently. Thus the invention is not limited to only those combinations shown herein, but rather may include other combinations.

What is claimed is:

1. A process for preparing a hydroxyalkyl carbamate comprising:

combining alkylene carbonate with anhydrous ammonia in the presence of an initiator compound and initially under at least partially evacuated conditions to form a reaction product comprising hydroxyalkyl carbamate; and wherein the alkylene carbonate has the formula:

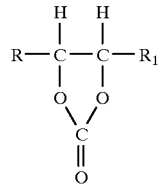

wherein R and $R^1$ are hydrogen or an alkyl, and in which at least one of R or $R^1$ is an alkyl.

2. The process of claim 1, wherein said reaction occurs at a pressure of less than about 75 psig.

3. The process of claim 1, further comprising removing at least a portion of unreacted anhydrous ammonia from the reaction product to form a hydroxyalkyl carbamate product.

4. The process of claim 3, wherein removing at least a portion of unreacted anhydrous ammonia from the reaction product forms a hydroxyalkyl carbamate product comprising greater than about 95% by weight of the hydroxyalkyl carbamate.

5. The process of claim 3, wherein removing at least a portion of unreacted anhydrous ammonia from the reaction product forms a hydroxyalkyl carbamate product comprising greater than about 97% by weight of the hydroxyalkyl carbamate.

6. The process of claim 1, wherein said combining occurs within a reaction vessel;

wherein said alkylene carbonate and said initiator compound are combined under at least partially evacuated conditions within said reaction vessel prior to combining said alkylene carbonate with said anhydrous ammonia; and wherein said reaction vessel is at least partially evacuated after combining said alkylene carbonate with said initiator compound in said reaction vessel and prior to combining said alkylene carbonate with said anhydrous ammonia.

7. The process of claim 1, wherein said alkylene carbonate is propylene carbonate and wherein said hydroxyalkyl carbamate is hydroxypropyl carbamate.

8. The process of claim 7, wherein said initiator compound comprises hydroxypropyl carbamate.

9. The process of claim 1, wherein said alkylene carbonate is butylene carbonate and wherein said hydroxyalkyl carbamate is hydroxybutyl carbamate.

10. The process of claim 9, wherein said initiator compound comprises hydroxybutyl carbamate.

11. The process of claim 1, wherein said initiator compound comprises at least one of hydroxalkyl carbamate, glycol ether, alcohol, or a mixture thereof.

12. The process of claim 1, wherein said initiator compound comprises hydroxalkyl carbamate.

13. The process of claim 1, wherein said combining occurs within a reaction vessel, and wherein said reaction vessel is at least partially evacuated prior to combining said alkylene carbonate with said anhydrous ammonia.

14. The process of claim 1, wherein said initiator compound comprises at least one of hydroxyalkyl carbamate, methyl alcohol, ethyl alcohol, or a mixture thereof.

15. The process of claim 1, wherein said combining occurs within a reaction vessel, and wherein said reaction vessel is sealed after combining said alkylene carbonate with said anhydrous ammonia.

16. The process of claim 1, wherein the alkylene carbonate and the anhydrous ammonia are initially combined at a vacuum of from about 0.1 mm Hg to about 50 mm Hg.

17. The process of claim 1, wherein the alkylene carbonate and the anhydrous ammonia are initially combined at a vacuum of from about 1 mm Hg to about 30 mm Hg.

18. The process of claim 1, wherein said reaction occurs at a pressure of less than about 90 psig.

19. A process for preparing hydroxypropyl carbamate comprising combining propylene carbonate with anhydrous ammonia in the presence of an intitiator compound and initially under at least partially evacuated conditions to form a reaction product comprising hydroxypropyl carbamate; wherein said reaction product is formed at a maximum pressure of less than about 90 psig.

20. The process of claim 19, wherein said combining occurs within a reaction vessel, and wherein said reaction vessel is at least partially evacuated prior to combining said propylene carbonate with said anhydrous ammonia.

21. The process of claim 19, wherein said intitiator compound comprises at least one of hydroxalkyl carbamate, glycol ether, alcohol, or a mixture thereof.

22. The process of claim 19, wherein said initiator compound comprises at least one of hydroxyalkyl carbamate, methyl alcohol, ethyl alcohol, or a mixture thereof.

23. The process of claim 19, wherein said intitiator compound comprises hydroxypropyl carbamate.

24. The process of claim 23, wherein said reaction product is formed at a pressure of less than about 75 psig.

25. The process of claim 23, wherein said propylene carbonate is initially combined with said anhydrous ammonia at a vacuum of from about 0.1 mm Hg to about 50 mm Hg.

26. The process of claim 23, further comprising removing at least a portion of unreacted anhydrous ammonia to form hydroxypropyl carbamate product comprising greater than about 95% by weight of said hydroxypropyl carbamate.

27. The process of claim 23, further comprising removing at least a portion of unreacted anhydrous ammonia to form hydroxypropyl carbamate product comprising greater than about 97% by weight of said hydroxypropyl carbamate.

28. The process of claim 23, wherein the propylene carbonate and the anhydrous ammonia are combined at a temperature of greater than about 60° C.

29. The process of claim 23, wherein the propylene carbonate and the anhydrous ammonia are combined at a temperature of greater than about 50° C.

30. The process of claim 23, wherein the butylene carbonate and the anhydrous ammonia are initially combined at a vacuum of from about 1 mm Hg to about 30 mm Hg.

31. The process of claim 23, wherein said combining occurs within a reaction vessel;
wherein said alkylene carbonate and said initiator compound are combined under at least partially evacuated conditions within said reaction vessel prior to combining said alkylene carbonate with said anhydrous ammonia; and
wherein said reaction vessel is at least partially evacuated after combining said alkylene carbonate with said initiator compound in said reaction vessel and prior to combining said alkylene carbonate with said anhydrous ammonia.

32. The process of claim 23, wherein said combining occurs within a reaction vessel, and wherein said reaction vessel is sealed after combining said alkylene carbonate with said anhydrous ammonia.

33. A process for preparing hydroxybutyl carbamate comprising combining butylene carbonate with anhydrous ammonia in the presence of an intitiator compound and initially under at least partially evacuated conditions to form a reaction product comprising hydroxybutyl carbamate; wherein said reaction product is formed at a maximum pressure of less than about 90 psig.

34. The process of claim 33, wherein the butylene carbonate and the anhydrous ammonia are combined in the presence of an initiator compound.

35. The process of claim 33, wherein said intitiator compound comprises at least one of hydroxalkyl carbamate, glycol ether, alcohol, or a mixture thereof.

36. The process of claim 33, wherein said initiator compound comprises at least one of hydroxyalkyl carbamate, methyl alcohol, ethyl alcohol, or a mixture thereof.

37. The process of claim 33, wherein said intitiator compound comprises hydroxybutyl carbamate.

38. The process of claim 37, wherein said reaction product is formed at a pressure of less than about 75 psig.

39. The process of claim 37, wherein the butylene carbonate and the anhydrous ammonia are initially combined at a vacuum of from about 0.1 mm Hg to about 50 mm Hg.

40. The process of claim 37, wherein the butylene carbonate and the anhydrous ammonia are combined at a temperature of greater than about 60° C.

41. The process of claim 37, wherein the butylene carbonate and the anhydrous ammonia are combined at a temperature of greater than about 50° C.

42. The process of claim 37, further comprising removing at least a portion of unreacted anhydrous ammonia to form hydroxybutyl carbamate product comprising greater than about 95% by weight of said hydroxybutyl carbamate.

43. The process of claim 37, further comprising removing at least a portion of unreacted anhydrous ammonia to form hydroxybutyl carbamate product comprising greater than about 97% by weight of said hydroxybutyl carbamate.

44. The process of claim 37, wherein said butylene carbonate is 1,2-butylene carbonate, and wherein said hydroxybutyl carbamate comprises a mixture of 2-hydroxylbutyl carbamate and 1-hydroxymethyl propyl carbamate.

45. The process of claim 44, wherein said reaction product comprises less than about 5% butylene glycol.

46. The process of claim 44, further comprising removing at least a portion of unreacted anhydrous ammonia to form hydroxybutyl carbamate product comprising greater than about 95% by weight of said hydroxybutyl carbamate.

47. The process of claim 44, further comprising removing at least a portion of unreacted anhydrous ammonia to form hydroxybutyl carbamate product comprising greater than about 99% by weight of said hydroxybutyl carbamate.

48. The process of claim 37, wherein the butylene carbonate and the anhydrous ammonia are initially combined at a vacuum of from about 1 mm Hg to about 30 mm Hg.

49. The process of claim 37, wherein said combining occurs within a reaction vessel, and wherein said reaction vessel is at least partially evacuated prior to combining said butylene carbonate with said anhydrous ammonia.

50. The process of claim 37, wherein said combining occurs within a reaction vessel;

wherein said alkylene carbonate and said initiator compound are combined under at least partially evacuated conditions within said reaction vessel prior to combining said alkylene carbonate with said anhydrous ammonia; and wherein said reaction vessel is at least partially evacuated after combining said alkylene carbonate with said initiator compound in said reaction vessel and prior to combining said alkylene carbonate with said anhydrous ammonia.

51. The process of claim 37, wherein said combining occurs within a reaction vessel, and wherein said reaction vessel is sealed after combining said alkylene carbonate with said anhydrous ammonia.

* * * * *